US009826910B2

(12) United States Patent
Burkett

(10) Patent No.: US 9,826,910 B2
(45) Date of Patent: Nov. 28, 2017

(54) SENSOR MOUNTING ASSEMBLY FOR SENSORED GUIDEWIRE AND ASSOCIATED DEVICES, SYSTEMS, AND METHODS

(71) Applicant: Volcano Corporation, San Diego, CA (US)

(72) Inventor: David H. Burkett, Temecula, CA (US)

(73) Assignee: VOLCANO CORPORATION, San Diego, CA (US)

( * ) Notice: Subject to any disclaimer, the term of this patent is extended or adjusted under 35 U.S.C. 154(b) by 45 days.

(21) Appl. No.: 14/551,463

(22) Filed: Nov. 24, 2014

(65) Prior Publication Data

US 2015/0148693 A1 May 28, 2015

Related U.S. Application Data

(60) Provisional application No. 61/907,855, filed on Nov. 22, 2013.

(51) Int. Cl.
*A61B 5/00* (2006.01)
*A61M 25/00* (2006.01)
(Continued)

(52) U.S. Cl.
CPC .......... *A61B 5/0215* (2013.01); *A61B 5/6851* (2013.01); *A61M 25/09* (2013.01);
(Continued)

(58) Field of Classification Search
CPC ................ A61B 5/6851; A61B 5/0215; A61B 2562/0247; A61M 25/09; A61M 2025/09083; A61M 2025/09166
See application file for complete search history.

(56) References Cited

U.S. PATENT DOCUMENTS 5,715,827 A * 2/1998 Corl ..................... A61B 5/0215
600/486
5,873,835 A * 2/1999 Hastings .............. A61B 5/0215
600/488

(Continued)

FOREIGN PATENT DOCUMENTS

WO          2011161212 A1      12/2011
WO     WO 2011-161212           12/2011

OTHER PUBLICATIONS

International Searching Authority/United States Patent Office, "Notification of Transmittal of the International Search Report and the Written Opinion of the International Searching Authority, or the Declaration," for PCT/US2014/067116, mailed Feb. 13, 2015, 10 pages.

(Continued)

*Primary Examiner* — Devin Henson

(57) ABSTRACT

Intravascular devices, systems, and methods are disclosed. In some embodiments, a guidewire system for treating a patient includes an internal sensor mount having a body and a first cutout extending through a wall of the body; a core wire secured to the internal sensor mount; a sensor assembly for detecting a physiological characteristic of a patient secured to the internal sensor mount; an external housing disposed about the internal sensor mount and including an opening in communication with the cutout of the internal sensor mount; a proximal flexible member secured to at least one of the internal sensor mount and the external housing; a first distal flexible member secured to at least one of the internal sensor mount and the external housing; and at least one conductor electrically coupled to the sensor assembly and extending proximally beyond the internal sensor mount through the proximal flexible member.

15 Claims, 10 Drawing Sheets

(51) Int. Cl.
*A61B 5/0215* (2006.01)
*A61M 25/09* (2006.01)

(52) U.S. Cl.
CPC ............... *A61B 2562/0247* (2013.01); *A61M 2025/09083* (2013.01); *A61M 2025/09166* (2013.01); *Y10T 29/49169* (2015.01)

(56) References Cited

U.S. PATENT DOCUMENTS

| | | |
|---|---|---|
| 7,097,620 B2 | 8/2006 | Corl et al. |
| 2006/0074318 A1 | 4/2006 | Ahmed et al. |
| 2007/0255145 A1* | 11/2007 | Smith .................. A61B 5/0215 600/485 |
| 2013/0102927 A1* | 4/2013 | Hilmersson .......... A61B 5/0215 600/585 |
| 2013/0218032 A1 | 8/2013 | Belleville |
| 2013/0237864 A1* | 9/2013 | Mazar .................. A61B 5/0215 600/488 |
| 2015/0074995 A1* | 3/2015 | Patil ................... A61B 5/02007 29/855 |

OTHER PUBLICATIONS

International Searching Authority/United States Patent Office, "Notification of Transmittal of the International Search Report and the Written Opinion of the International Searching Authority, or the Declaration," for PCT/US2014/066390, mailed Feb. 13, 2015, 10 pages.

* cited by examiner

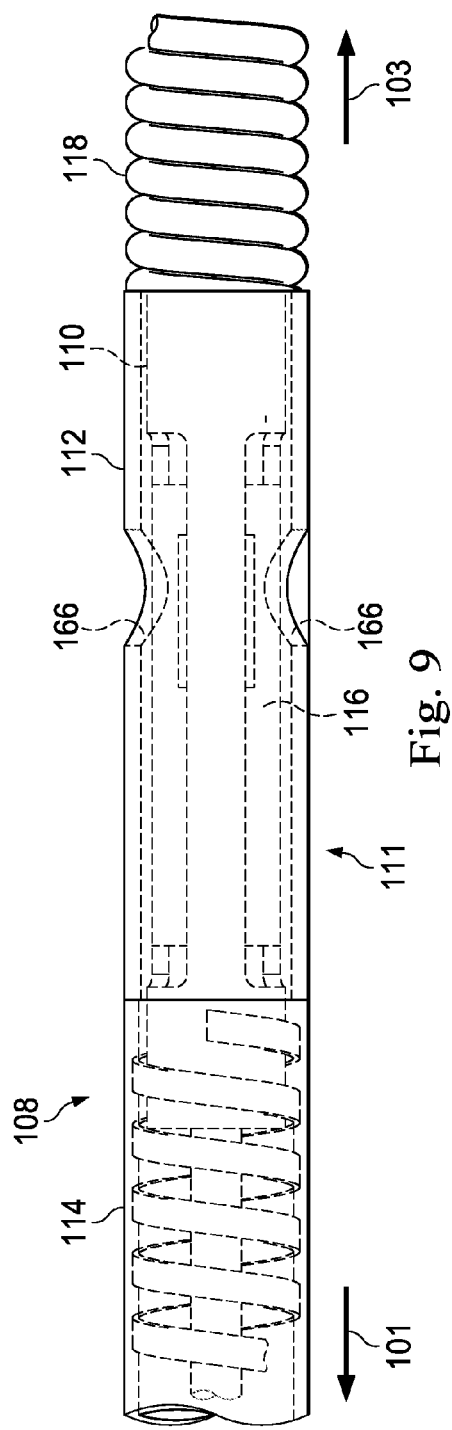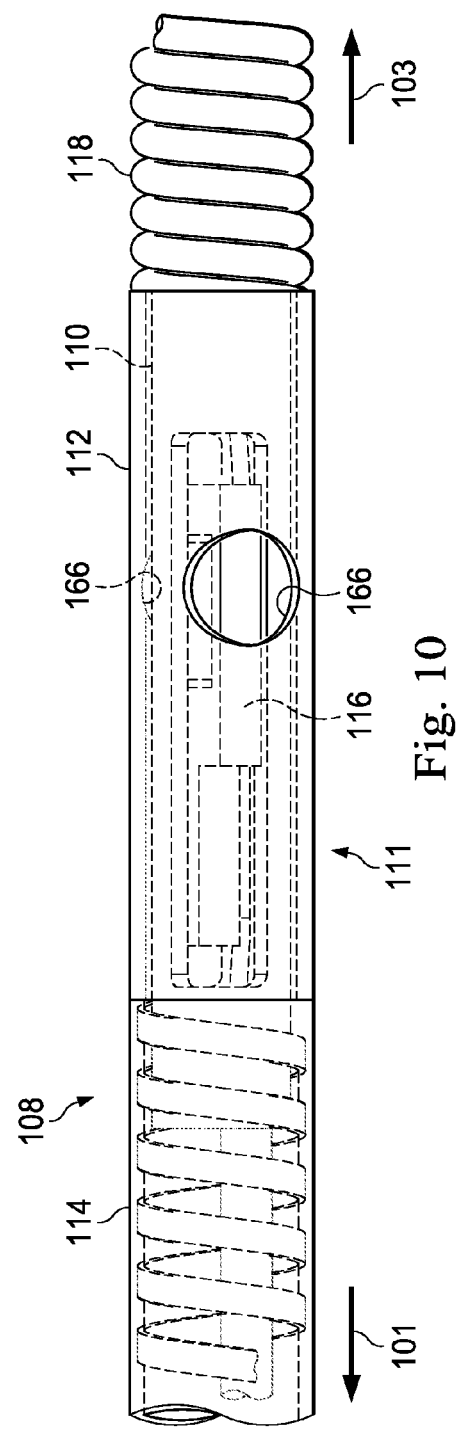

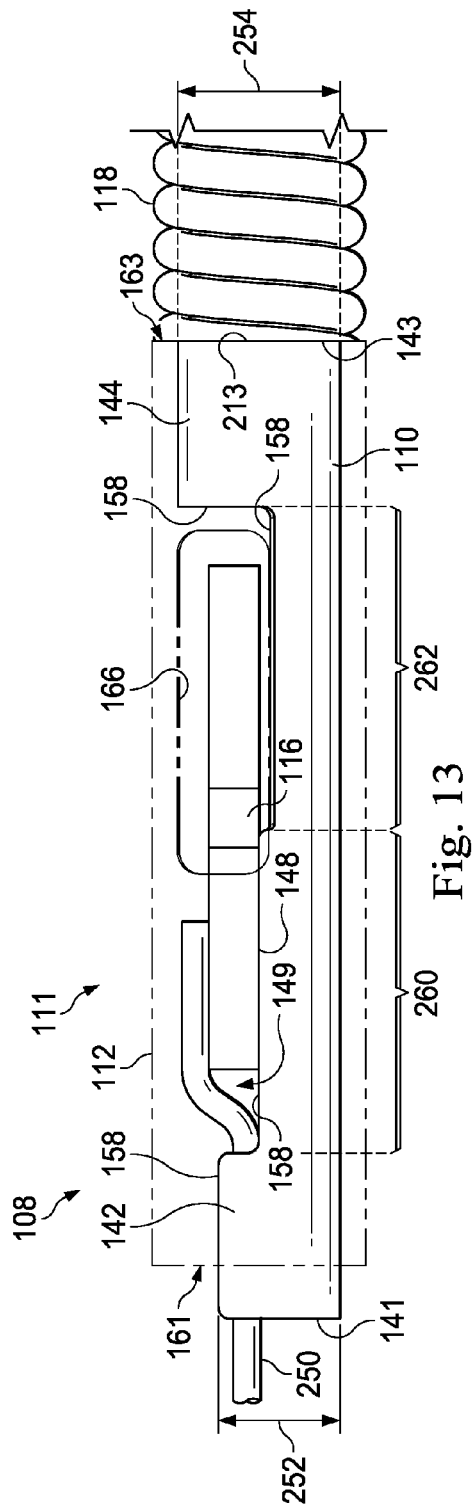
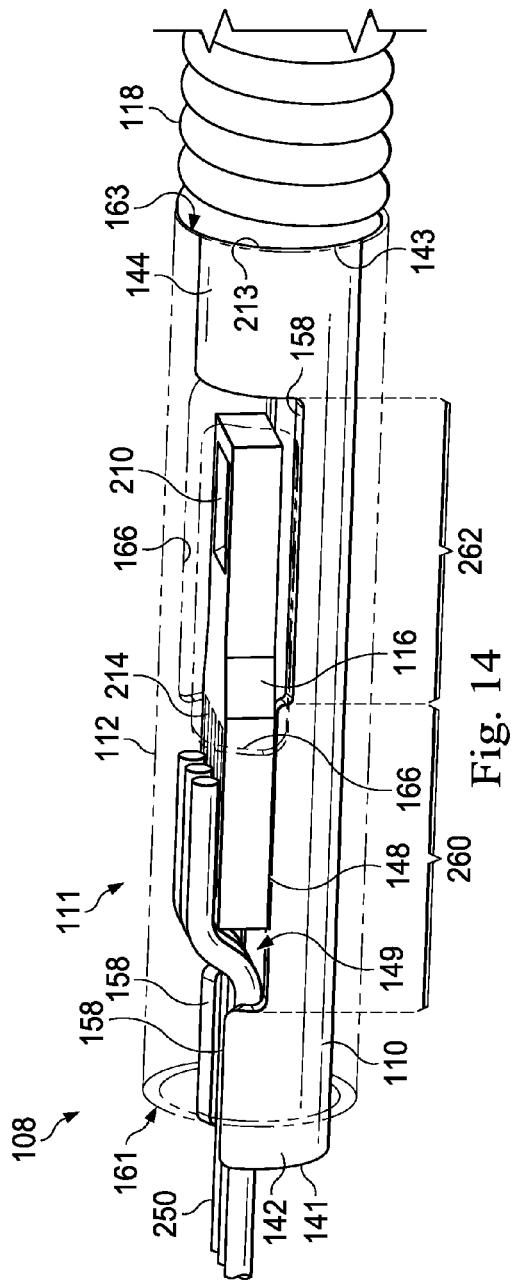
Fig. 13
Fig. 14

SENSOR MOUNTING ASSEMBLY FOR SENSORED GUIDEWIRE AND ASSOCIATED DEVICES, SYSTEMS, AND METHODS

CROSS REFERENCE TO RELATED APPLICATION

The present application claims priority to and the benefit of the U.S. Provisional Patent Application No. 61/907,855, filed Nov. 22, 2013, which is hereby incorporated by reference in its entirety.

TECHNICAL FIELD

The present disclosure relates to intravascular devices, systems, and methods. In some aspects the present disclosure relates to intravascular devices, systems, and methods that include a sensor mounting assembly with an internal sensor mount and an external housing.

BACKGROUND

With the advent of angioplasty, pressure measurements have been taken in vessels and particularly in coronary arteries for the treatment of certain ailments or conditions. Typically in the past, such pressure measurements have been made by measuring the pressure at a proximal extremity of a lumen provided in a catheter advanced into the coronary artery of interest. Such an approach has, however, been less efficacious as the diameters of the catheters became smaller with the need to advance the catheter into smaller vessels and to the distal side of atherosclerotic lesions. This made necessary the use of smaller lumens that gave less accurate pressure measurements and in the smallest catheters necessitated the elimination of such a pressure lumen entirely. Furthermore, the catheter is large enough to significantly interfere with the blood flow and damp the pressure resulting in an inaccurate pressure measurement. In an attempt to overcome these difficulties, ultra miniature pressure sensors have been proposed for use on the distal extremities of a guidewire. Using a guidewire with a smaller diameter is less disruptive to the blood flow and thus provides an accurate pressure reading.

However, the manufacturing process to consistently locate miniature sensors in guidewires can be challenging. For example, because of their size, current sensors on guidewires are mounted by hand in a housing cutout or mounted along a core wire. However, the optimal alignment of the sensor is dependent upon an assembler's ability to align the sensor within a given design. Because the sensors are often placed by hand, there is frequently some variability in sensor location from guidewire to guidewire. This variability may be compounded when sensors are located or placed by different workers. After being mounted, sensors are also susceptible to damage during further guidewire manufacturing steps.

Accordingly, there remains a need for improved devices, systems, and methods that have a capacity for increased consistency among workers even when the systems, devices, and methods are performed by hand. There is also a need to prevent damage to mounted sensors during additional guidewire manufacturing steps. The present disclosure addresses one or more of the problems in the prior art.

SUMMARY

Embodiments of the present disclosure are directed to intravascular devices, systems, and methods including a guidewire having a sensor mounting assembly with an internal sensor mount to which a sensor assembly is mounted and an external housing surrounding the internal sensor mount.

In an exemplary aspect, the present disclosure is directed to a guidewire system for treating a patient including an internal sensor mount having a body and a first cutout extending through a wall of the body; a core wire secured to the internal sensor mount; a sensor assembly for detecting a physiological characteristic of a patient secured to the internal sensor mount; an external housing disposed about the internal sensor mount and including an opening in communication with the cutout of the internal sensor mount; a proximal flexible member secured to at least one of the internal sensor mount and the external housing; a first distal flexible member secured to at least one of the internal sensor mount and the external housing; and at least one conductor electrically coupled to the sensor assembly and extending proximally beyond the internal sensor mount through the proximal flexible member.

In an aspect, the internal sensor mount includes a second cutout extending through the wall of the body. In an aspect, the internal sensor mount includes a support member disposed between the first and second cutouts. In an aspect, the sensor assembly is mounted on rails defined by the first and second cutouts of the internal sensor mount. In an aspect, the interior of the internal sensor mount includes a first filling layer including solder, an adhesive, or a combination thereof, and a second filling layer including solder, an adhesive, or a combination thereof, the second layer being disposed over the first layer and defining a mounting surface such that the mounting surface is disposed higher than the rails, and wherein the sensor assembly is mounted on the mounting surface. In an aspect, an interior of the internal sensor mount includes a mounting surface defined by solder, an adhesive, or a combination thereof, the sensor assembly being mounted on the mounting surface. In an aspect, the external housing includes a plurality of openings configured to provide fluid communication between the sensor assembly and an environment outside the external housing. In an aspect, the internal sensor mount is formed of stainless steel. In an aspect, the guidewire system further includes a second distal flexible member secured to at least one of the internal sensor mount, the external housing, and the first distal flexible member. In an aspect, at least one of the proximal flexible member, the external housing, the first distal flexible member, and the second distal flexible member is formed of a radiopaque material. In an aspect, the external housing and the first distal flexible member are formed of a radiopaque material, and wherein the second distal flexible member is formed of a non-radiopaque material and disposed between the external housing and the first distal flexible member. In an aspect, the external housing is formed of a radiopaque material, and wherein the proximal flexible member includes a first segment and a second segment, the second segment being formed of a radiopaque material and the first segment being formed of a non-radiopaque material, wherein the first segment is disposed between the external housing and the second segment.

In another exemplary aspect, the present disclosure is directed to a method of building a guidewire including securing a core wire to an internal sensor mount; securing a sensor assembly within the internal sensor mount; advancing a proximal flexible member over the internal sensor mount; securing an external housing and a first distal flexible member to the internal sensor mount; and securing the proximal flexible member to the internal sensor mount.

In an aspect, securing an external housing and a first distal flexible member to the internal sensor mount includes securing the external housing to the first distal flexible member to form a subcomponent; and securing the subcomponent to the internal sensor mount. In an aspect, securing the subcomponent to the internal sensor mount includes advancing the subcomponent in a proximal direction relative to the internal sensor mount such that at least a portion of the first distal flexible member contacts the internal sensor mount. In an aspect, securing an external housing and a first distal flexible member to the internal sensor mount includes securing the external housing to the internal sensor mount separately from securing the first distal flexible member to the internal sensor mount. In an aspect, advancing the proximal flexible member over the internal sensor mount includes advancing the proximal flexible member in a proximal direction relative to the internal sensor mount from a distal end of the internal sensor mount. In an aspect, the method further includes after securing the external housing to the internal sensor mount, advancing the proximal flexible member in a distal direction relative to the internal sensor mount such that at least a portion of the proximal flexible member contacts the external housing. In an aspect, securing a sensor assembly within the internal sensor mount includes: engaging the sensor assembly and an edge of a cutout in the internal sensor mount. In an aspect, securing a core wire to an internal sensor mount includes aligning a reduced profile portion of the core wire with the internal sensor mount. In an aspect, securing a sensor assembly within the internal sensor mount further includes seating the sensor assembly on solder, an adhesive, or a combination thereof disposed within the internal sensor mount. In an aspect, securing the external housing and the first distal flexible member to the internal sensor mount includes bringing an opening of the external housing into communication with a cutout of the internal sensor mount. In an aspect, the method further includes securing a second distal flexible member to at least one of the external housing, the first distal flexible member, and internal sensor mount.

BRIEF DESCRIPTION OF THE DRAWINGS

Illustrative embodiments of the present disclosure will be described with reference to the accompanying drawings, of which:

FIG. 9 illustrates a top view of a distal portion of the guidewire of FIG. 2 according to an exemplary aspect of the present disclosure.

FIG. 10 illustrates a perspective side view of a distal portion of the guidewire of FIG. 2 according to an exemplary aspect of the present disclosure.

FIG. 13 illustrates a side view of a distal portion of the guidewire of FIG. 2 according to an exemplary aspect of the present disclosure.

FIG. 14 illustrates a perspective side view of a distal portion of the guidewire of FIG. 2 according to an exemplary aspect of the present disclosure.

DETAILED DESCRIPTION

Figure 1:
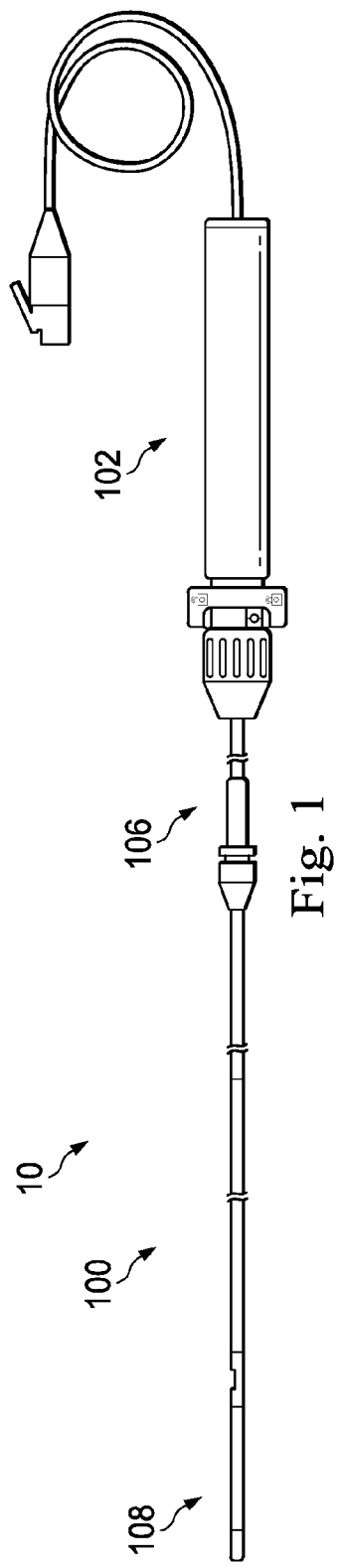
FIG. 1 is a diagrammatic side view of a guidewire system according to an exemplary embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any connections and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The devices, systems, and methods disclosed herein include a guidewire with a sensor mounting assembly that is configured to increase the repeatability and consistency of sensor placement during the manufacturing process. The sensor mounting assembly includes an internal sensor mount and an external housing. In some embodiments, the sensor mounting assembly is arranged to enable a worker to reference the internal sensor mount when placing the sensor to identify an axial, lateral, and/or vertical position to increase consistency of assembly from guidewire to guidewire even among different workers. Some sensor mounting assembly embodiments allow a worker to locate the sensor in axial, lateral, and/or vertical directions. Accordingly, guidewires may be assembled with increased reliability and consistency. The guidewire having sensing capabilities may be adapted to be used in connection with a patient lying on a table or a bed in a cath lab of a typical hospital in which a catheterization procedure such as for diagnosis or treatment is being performed on the patient.

FIG. 1 shows an exemplary guidewire system 10 consistent with the principles disclosed herein. The guidewire system 10 in this embodiment is configured to sense or detect a physiological characteristic of a condition of the patent. For example, it may detect or sense a characteristic of the vasculature through which it has been introduced. In one embodiment, the guidewire system 10 has pressure sensing capabilities. The guidewire system 10 includes a guidewire 100 and a connector 102 coupled to a proximal end of the guidewire 100. The connector 102 in this example in FIG. 1 is configured to communicate with the guidewire 100, serve as a graspable handle to enable the surgeon to easily manipulate the proximal end of the guidewire 100, and connect to a console or further system with a modular plug. Accordingly, because the guidewire 100 is configured to detect physiological environmental characteristics, such as pressure in an artery, for example, data or signals representing the detected characteristics may be communicated from the guidewire 100, through the connector 102, to a console or other system for processing. In this embodiment, the connector 102 is configured to selectively connect to and disconnect from the guidewire 100. In some embodiments, the guidewire system 10 is a single-use device. The guidewire 100, in the embodiment shown, is selectively attachable to the connector 102 and includes a proximal portion 106 connectable to the connector 102 and a distal portion 108 configured to be introduced to a patient during a surgical procedure.

Figure 2:
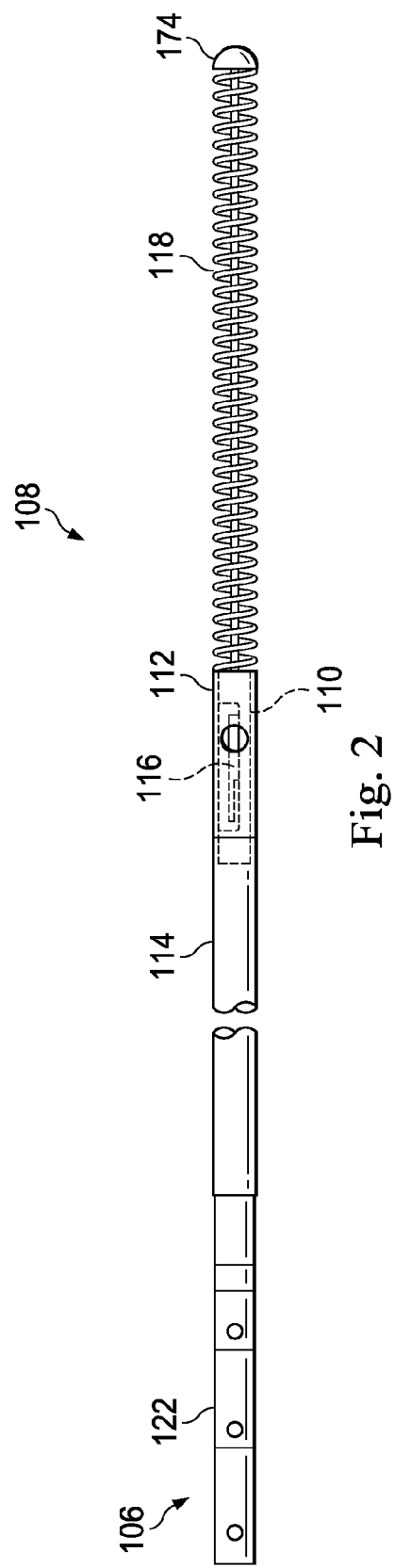
FIG. 2 is a diagrammatic perspective view of a guidewire according to an exemplary embodiment of the present disclosure.
Figure 3:
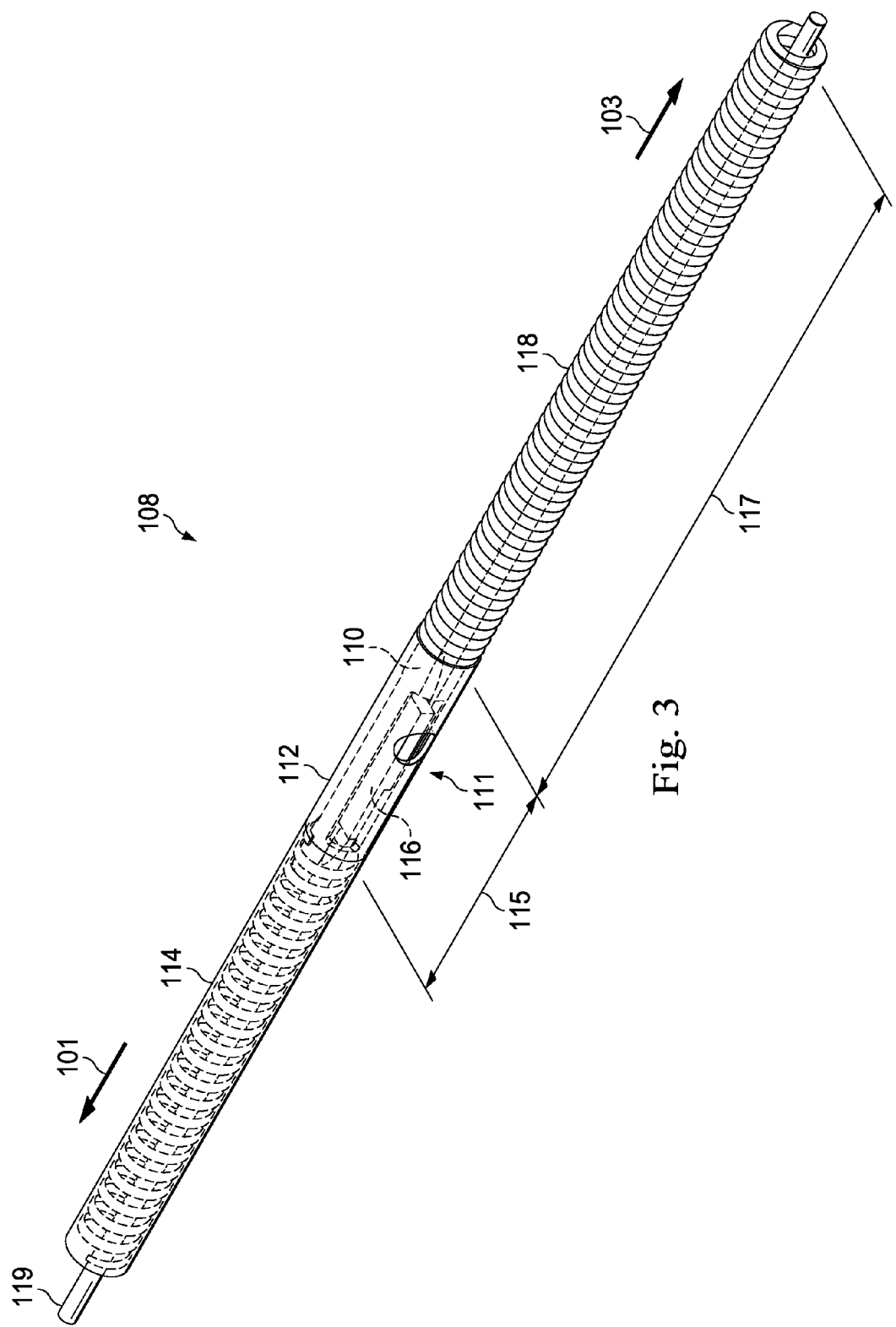
FIG. 3 illustrates a perspective view of a distal portion of the guidewire of FIG. 2 according to an exemplary aspect of the present disclosure.
Figure 4:
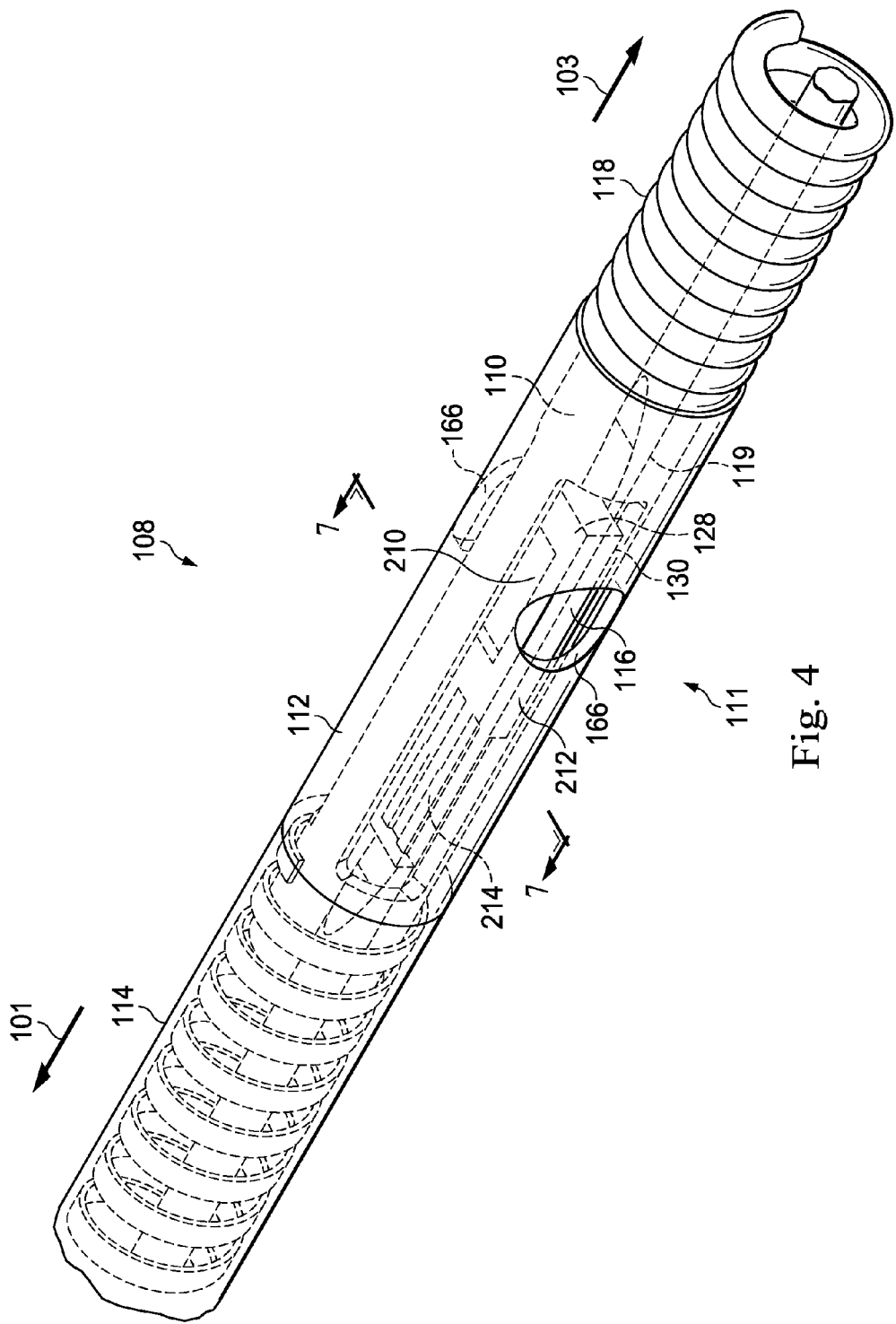
FIG. 4 illustrates a perspective view of a section of the distal portion of the guidewire of FIG. 3 according to an exemplary aspect of the present disclosure.

The following discussion generally refers to FIGS. 2, 3, and 4. FIG. 2 shows the entire guidewire 100, FIG. 2 shows the distal portion 108 of guide 100, and FIG. 3 shows a sensor mounting assembly 111 at the distal portion 108 of guidewire 100. The guidewire 100 includes an internal sensor mount 110, an external housing 112, a proximal flexible member 114, a sensor assembly 116, a distal flexible member 118, and a proximal electrical interface 122.

The proximal electrical interface 122 is configured to electrically connect the sensor assembly 116 and the connector 102 in order to ultimately communicate signals to the processing system. In accordance with this, the electrical interface 122 is in electrical communication with the sensor assembly 116 and in this embodiment is configured to be received within the connector 102. The electrical interface 122 may include a series of conductive contacts on its outer surface that engage and communicate with corresponding contacts on the connector 102.

The sensor assembly 116 includes a a sensor block 212. Sensor assembly 116 is configured to include conductors that extend from the sensor block 212 to the proximal electrical interface 122. The sensor assembly 116 is arranged and configured to measure a physiological characteristic of a patient. When used on the guidewire 100, the sensor assembly 116 is arranged and configured to measure a physiological characteristic of a vessel itself, such as a vascular vessel. In one embodiment, the sensor assembly 116 includes a pressure transducer configured to detect a pressure within a portion of a patient, such as the pressure within a blood vessel. In another embodiment, the sensor assembly 116 is a flow sensor that may be used to measure flow through the vessel. In yet other embodiments, the sensor assembly 116 includes a plurality of sensors arranged to detect one or more characteristics of the patient and provide feedback or information relating to the detected physiological characteristic(s). The sensor assembly 116 may be disposed, for example, less than about 5 cm from the distal-most end 174 of the guidewire 100. In one embodiment, the sensor assembly 116 is disposed about 3 cm from the distal-most end 174 of the guidewire 100.

Figure 7:
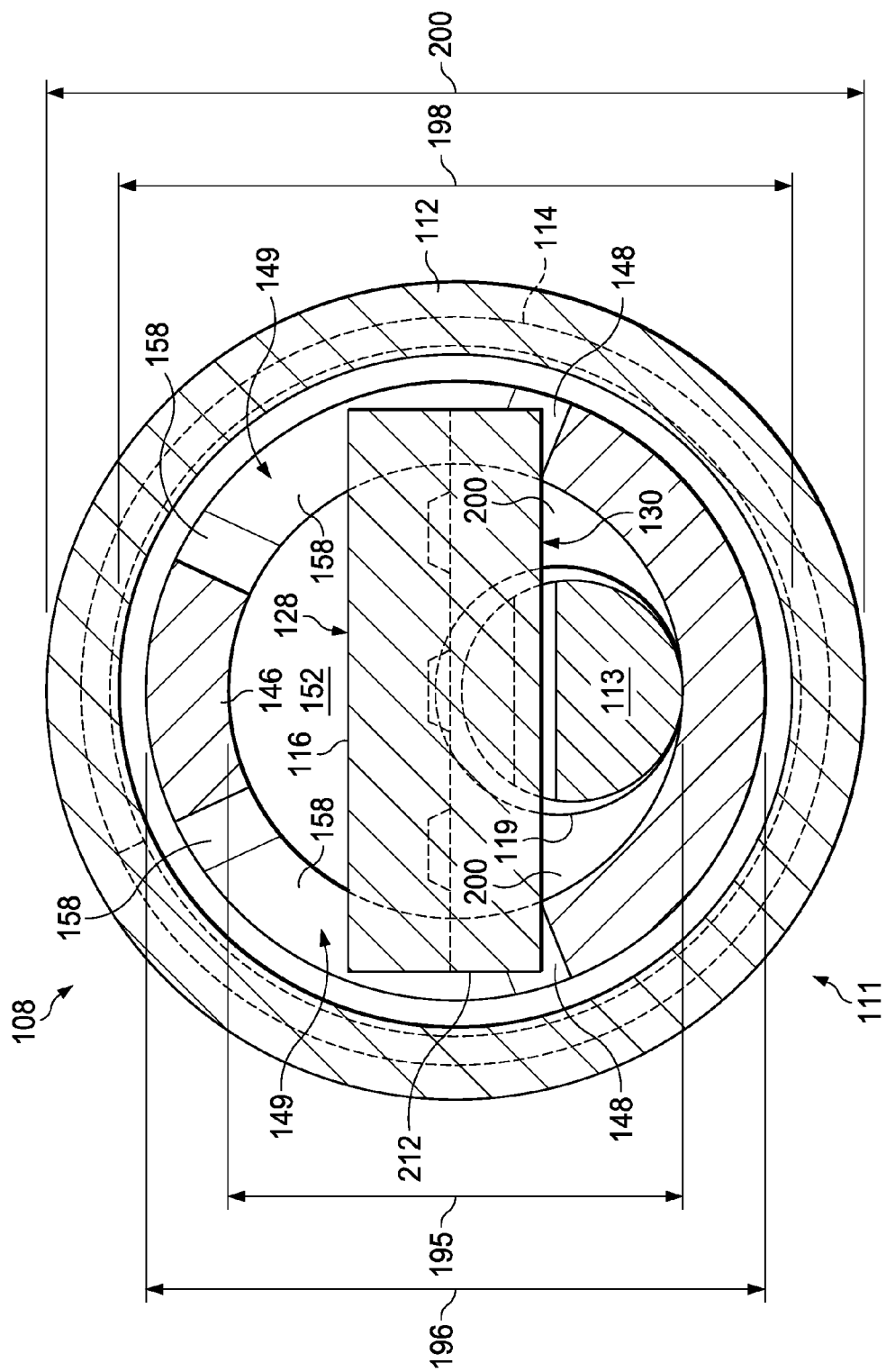
FIG. 7 illustrates a cross-sectional axial view of the distal portion of the guidewire of FIG. 2 along line 7-7 of FIG. 4 according to an exemplary aspect of the present disclosure.

The sensor block 212 includes the diaphragm 210 and can include, for example, a wafer, a chip, or other transducer carrying substrate. The sensor block 212 in this embodiment is configured to include the diaphragm 210 and configured to have contacts or conductive connectors 214 for electrical communication with the conductors that extend to the proximal electrical interface 122. The sensor block 212 in this embodiment is sized to fit within the diametric profile of the guidewire 100. In the embodiment shown, the sensor block 212 is relatively rectangular shaped, and includes a sensor side 128 and an interface side 130 (FIG. 7). While the top side of the sensor block 212 is described as the sensor side, it is understood in various embodiments, diaphragm 210 can be disposed on sensor side 128, interface side 130, and/or a lateral side of sensor block 212. The interface side 130 is configured to engage and/or contact a portion of the internal sensor mount 110 in some embodiments. In some embodiments, the interface side 130 is configured to be in contact with an adhesive positioned between the sensor block 212 and the internal sensor mount 110.

The sensor block 212 may be sized to have an axial length in the range of about 0.020 to 0.055 inch. In one embodiment, the axial length is about 0.035 inch. The width may be in the range of about 0.004 to 0.015 inch. In one embodiment, the width is about 0.009 inch. The height may be in the range of about 0.001 to 0.008 inch. In one embodiment, the height is about 0.003 inch. Other sizes of sensor blocks are contemplated. The contacts 214 on the sensor block 212 may be formed at the proximal end and may be shaped to electrically couple with the conductors in communication with the proximal electrical interface 122. In the embodiment shown, the contacts 214 are disposed along a bottom surface of sensor assembly 116, on the opposite side as the diaphragm 210. In alternative embodiments, the contacts 214 are disposed on the same side as the diaphragm 210. For example, sensor assembly 116 can include a sensor having the contacts 214 on the same side as the diaphragm 210.

In some embodiments, the guidewire 100 includes conductors that extend from the contacts 214 to the proximal electrical interface 122 (FIG. 2). In some embodiments, the conductors are electrical cables or wires extending from the sensor assembly 116. The conductors are configured to extend from the top or bottom of the sensor block 212 rearward to the edge of the sensor block 212, and then bend to extend and enter the inner lumen of the internal sensor mount 110. In some embodiments, the conductors are integrated with a core wire 119, which can extend along a length of guidewire 100. In some embodiments, three conductors are provided; however, the number of conductors in any particular embodiment may depend in part on the type or number of sensors disposed within the guidewire 100. For example, the number of conductors can be in the range of about one to twenty conductors, one to ten conductors, one to five conductors, one to four conductors, one to three conductors, etc. In some embodiments, the conductors are soldered to the contacts 214 on the sensor block 212 during the manufacturing process. A sealant or adhesive may be used to isolate and protect the connections of the conductors and the contacts 214. Accordingly, the conductors may carry signals to and from the sensor assembly 116.

The internal sensor mount 110 is formed of a suitable biocompatible material. In some embodiments, the internal sensor mount 110 is formed of stainless steel and/or metal alloy. For example, a high tensile 304V stainless steel may be used. Using stainless steel can advantageously improve structural integrity of the internal sensor mount 110 and be cost-efficient for producing the internal sensor mount. Materials including, e.g., a Nitinol alloy may be used in different embodiments. Other materials would be apparent to one of ordinary skill in the art. In some embodiments, the material (s) provide sufficient stiffness to minimize the likelihood that the internal sensor mount 110 unintentionally bends during assembly and/or use.

In some embodiments, an outer diameter 196 (FIG. 7) of the internal sensor mount 110 is smaller than an inner diameter 195 (FIG. 7) of the external housing 112 such that the external housing 112 can be disposed around internal sensor mount 110. In some embodiments, the internal sensor mount 110 has outer diameter 196 of, for example, 0.025 inch or less and has a suitable wall thickness of, for example, 0.001 inch to 0.005 inch, for example. Where a smaller guidewire is desired, the internal sensor mount 110 can have exterior diameter 196 of 0.012 inch or less. Some embodiments of the guidewire system 10 use large-diameter internal sensor mounts having outer diameter 196 in the range of about, for example, 0.015 inch to 0.030 inch. As such, the internal sensor mount 110 may have an outer diameter 196 in the range of about 0.030 inch or less. In some embodiments, the inner diameter 195 (FIG. 7) may be 70%-80% of the size of the outer diameter 196. For example, a 0.0105 inch outer diameter 196 may have an inner diameter 195 of about 0.007 inch. Yet other sizes are also contemplated. In the embodiment shown, the smaller outer diameter 196 may help the internal sensor mount act as an alignment feature that enables a worker to properly locate the sensor assembly with reference to the internal sensor mount. In some embodiments, the internal sensor mount 110 has a length between about 0.030 inch and 0.500 inch, or between about 0.050 inch and 0.075 inch, although other lengths are contemplated.

The external housing 112 is positioned between the proximal flexible member 114 and the distal flexible member 118, and is configured to cover and protect the sensor assembly 116. As such, the external housing 112 covers the internal sensor mount 110 and defines a chamber in which the internal sensor mount 110 resides. The external housing 112 can be configured to reinforce the internal sensor mount 110. The external housing 112 has a longitudinal extent or length 115. Because the stiffness of the internal sensor mount 110 may be decreased by one or more cutouts (as described herein), the external housing 112 may be configured to restore the rigidity of the internal sensor mount 110 and/or the sensor mounting assembly 111 in general. In the embodiment shown, it does this by extending over at least a portion of the longitudinal extent spanned by internal sensor mount 110. The external housing 112 may be formed of a rigid material, such as a stainless steel, a Nitinol alloy, palladium, a tungsten platinum alloy, and/or other biocompatible material that provides rigidity to the sensor mount region of the internal sensor mount 110. In some embodiments, the external housing 112 is formed of a radiopaque material or includes a radiopaque coating.

Figure 5:
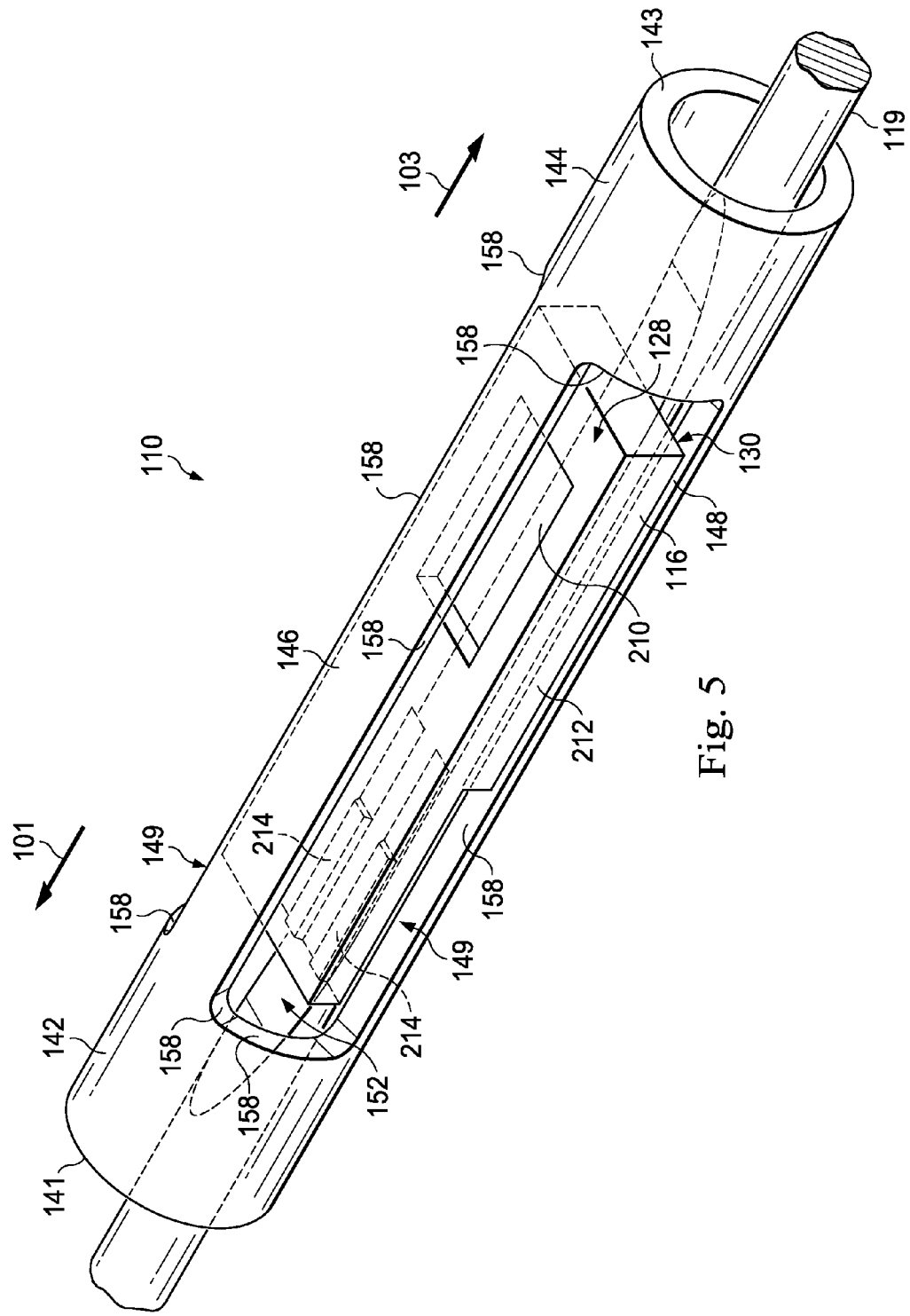
FIG. 5 illustrates a perspective view of an internal sensor mount and a sensor assembly of the guidewire of FIG. 2 according to an exemplary aspect of the present disclosure.

One or more openings 166 in the external housing 112 provide fluid communication between the sensor assembly 116 in the chamber formed by external housing 112 and the outer environment. In some embodiments, the one or more openings 166 are formed to lie laterally beside or adjacent to the diaphragm 210 (FIG. 5). The one or more openings 166 are sized and configured so that the detected physiological characteristic at the sensor in the chamber formed by external housing 112 equates to the environmental characteristic outside the external housing 112. For example, when the sensor assembly 116 is a pressure sensor, the one or more openings 166 are sized so that the pressure in the chamber formed by external housing 112 about the pressure sensor is substantially the same as the pressure outside the chamber.

In the illustrated embodiments, the sensor mounting assembly 111 includes generally cylindrically-shaped components (e.g., internal sensor mount 110, external housing 112, etc.). Some embodiments of the sensor mounting assembly 111 include one or more non-cylindrical components (e.g., internal sensor mount 110, external housing 112, etc.). Accordingly, the cross-section of the sensor mounting assembly 111 may form an ellipse or other shape. In one embodiment, an elliptical shape of the external housing 112 accommodates sensor blocks that have a width greater than the outer profile of the internal sensor mount 110.

The proximal flexible member 114 extends proximally from the internal sensor mount 110 toward the proximal electrical interface 122. In the exemplary embodiment shown, the proximal flexible member 114 is formed of a biocompatible polymeric material, such as Pebax®, for example, in order to reduce friction incurred as the guidewire is introduced through vessels in the body. Other materials may be used. Depending on the embodiment, the proximal flexible member 114 may have a thickness of about 0.001" to 0.002", although other thicknesses are contemplated. For example, proximal flexible member 114 can have a thickness in the range between about 0.001" and 0.040", 0.001" and 0.020", 0.001" and 0.010", and 0.001" and 0.005". In the example shown, the sleeve may include a hydrophilic coating that also lubricates and enables low friction passage through the vessels. In some embodiments, proximal flexible member 114 is a coil-embedded polymer sleeve (for, e.g., improved hoop strength). In other embodiments, proximal flexible member 114 can be at least one of a coil and a polymer sleeve.

In some embodiments, proximal flexible member 114 can include a radiopaque material. In some embodiments, proximal flexible member 114 can include multiple radiopaque segments that are separated from each other by non-radiopaque segments. For example, the proximal flexible member 114 can include a first segment and a second segment. The first segment can be positioned proximal of and adjacent to the external housing 112 while the second segment can be positioned proximal of and adjacent to the first segment. The second segment can include a radiopaque material while the first segment does not. In some embodiments, the external housing 112 includes a radiopaque material and can be one radiopaque marker among others. Thus, on a proximal side of the external housing 112, a radiopaque second segment and a radiopaque external housing 112 can be separated by a non-radiopaque first segment. Such an arrangement can be used as part of a marker system to readily identify the location of the sensor assembly 116.

The distal flexible member 118 can include a coil and a distal-most end 174. The distal-most end 174 may be defined by a solder ball, cap, or other suitable structure. The distal-most end 174 has a leading rounded end that can smoothly slide against tissue as the guidewire 100 is fed through the vasculature of a patient. In some embodiments, the distal-most end 174 is a solder joint with a rounded end. In other embodiments, the distal-most end 174 is defined by a separate component secured to the coil of distal flexible member 118 via an adhesive, welding, and/or other attachment method. In some embodiments, the distal flexible member 118 can be a polymer section without a coil or disposed over the top of and/or around a coil.

The coil of distal flexible member 118 extends from the internal sensor mount 110 and/or external housing 112 in the distal direction to the distal-most end 174. The coil may be a coil spring formed of a suitable material including stainless steel, Nitinol, palladium, a tungsten platinum alloy, and/or other biocompatible material, for example. In that regard, the coil may be formed of suitable material including a radiopaque material, or the coil may include a radiopaque coating. In some embodiments, the coil of distal flexible member 118 has an outside diameter of between about 0.001" and 0.020", 0.001" and 0.010", 0.010" and 0.020", etc. For example, the coil can have an outer diameter of 0.014", 0.018", etc. In one embodiment, the coil is formed from a wire having a diameter of 0.003". A proximal end 213 (FIG. 8) of the distal flexible member 118 and/or the coil is connected or attached, such as by solder, threading, combinations thereof, and/or otherwise coupled onto a distal end 163 (FIG. 8) of the external housing 112 and/or a distal end 143 of the internal sensor mount 110. In some embodiments, the distal flexible member 118 and/or the coil have a length 117 within a range of about 1 cm to 30 cm, although other ranges are contemplated. The distal flexible member 118 and/or the coil have a length 117 of approximately 3 cm in some instances.

In some embodiments, the distal flexible member 118 includes two coils, one of which is radiopaque and one of which is not radiopaque. For example, a second coil can be disposed between the external housing 112/internal sensor mount 110 and a first coil such that the distal end 163 of the external housing 112 and/or the distal end 143 of the internal sensor mount 110 engages the second coil. The second coil can have a length between about 0.5 cm and 30 cm, 1 cm and 10 cm, 1 cm and 5 cm, 1 cm and 4 cm, etc. The second coil has a length of 1.5 cm in one embodiment. The second coil can be formed of a suitable material including stainless steel, Nitinol, palladium, a tungsten platinum alloy, and/or other biocompatible material. In some embodiments, the second coil is not radiopaque. Thus, in some embodiments, the distal portion 108 of guidewire 100 includes the first coil that is radiopaque, followed by the second coil that is not radiopaque, and a radiopaque external housing 112.

In some embodiments, multiple radiopaque coils or flexible members are arranged such that each radiopaque component is separated from another radiopaque component by a non-radiopaque material. Such an arrangement provides a reliable marker system for visualizing where the sensor is located. The marker system can include radiopaque markers of known lengths (e.g., the external housing 112 and/or the first coil) that are spaced apart by a known length (e.g., by a non-radiopaque second coil.) The position of the sensor assembly 116 relative to the external housing 112 is also known (e.g., distance from a proximal end 161 and/or distal end 163 of external housing 112. Thus, using the marker system with components of known lengths, the relative position of the sensor assembly 116 within the patient's vasculature can be determined. As a result, the measurements obtained by the sensor assembly 116 can be directly correlated with specific portions of the patient's vasculature, which can improve the evaluation of the vasculature and corresponding treatment planning. Aspects of the arrangement are also compatible with one or more software protocols for image processing, intravascular guidance systems, etc. As described above, in some embodiments, the external housing 112 can include a radiopaque material and can be one marker among others in a marker system. Such a marker system can include components that are proximal and/or distal to the sensor assembly 116. In other embodiments, the radiopaque external housing 112 is the proximal end of the distal radiopaque tip (including, e.g., the external housing 112 and the distal flexible member 118).

Figure 6:
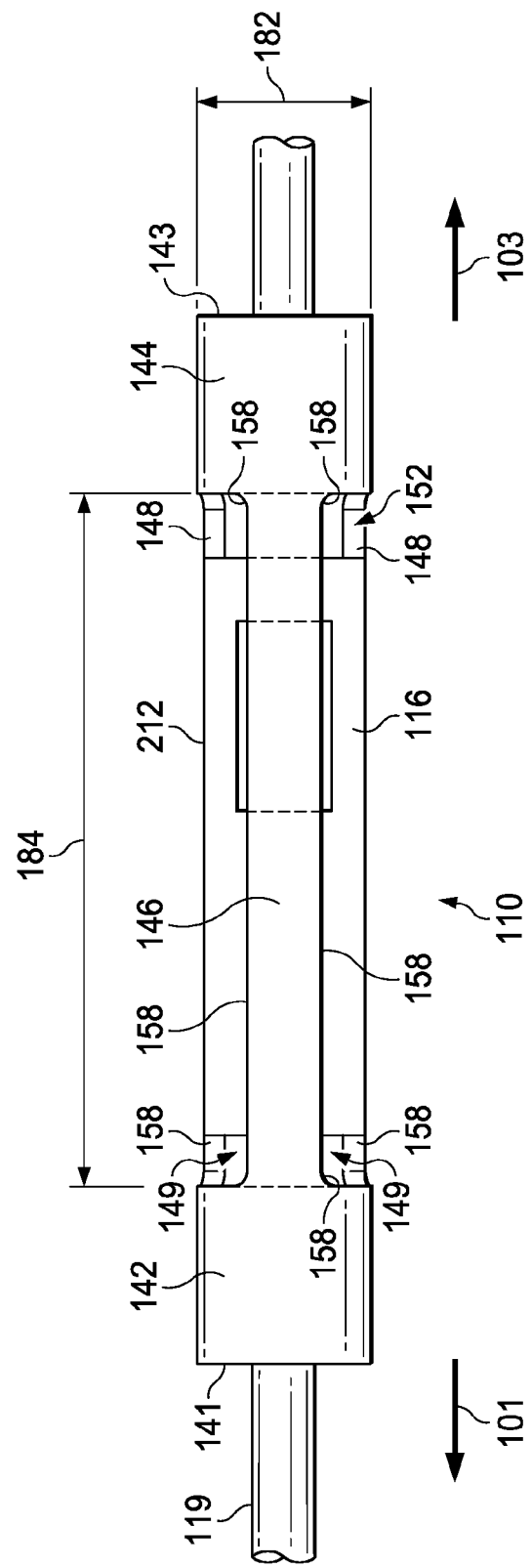
FIG. 6 illustrates a top view of the internal sensor mount and the sensor assembly of the guidewire of FIG. 2 according to an exemplary aspect of the present disclosure.
Figure 8:
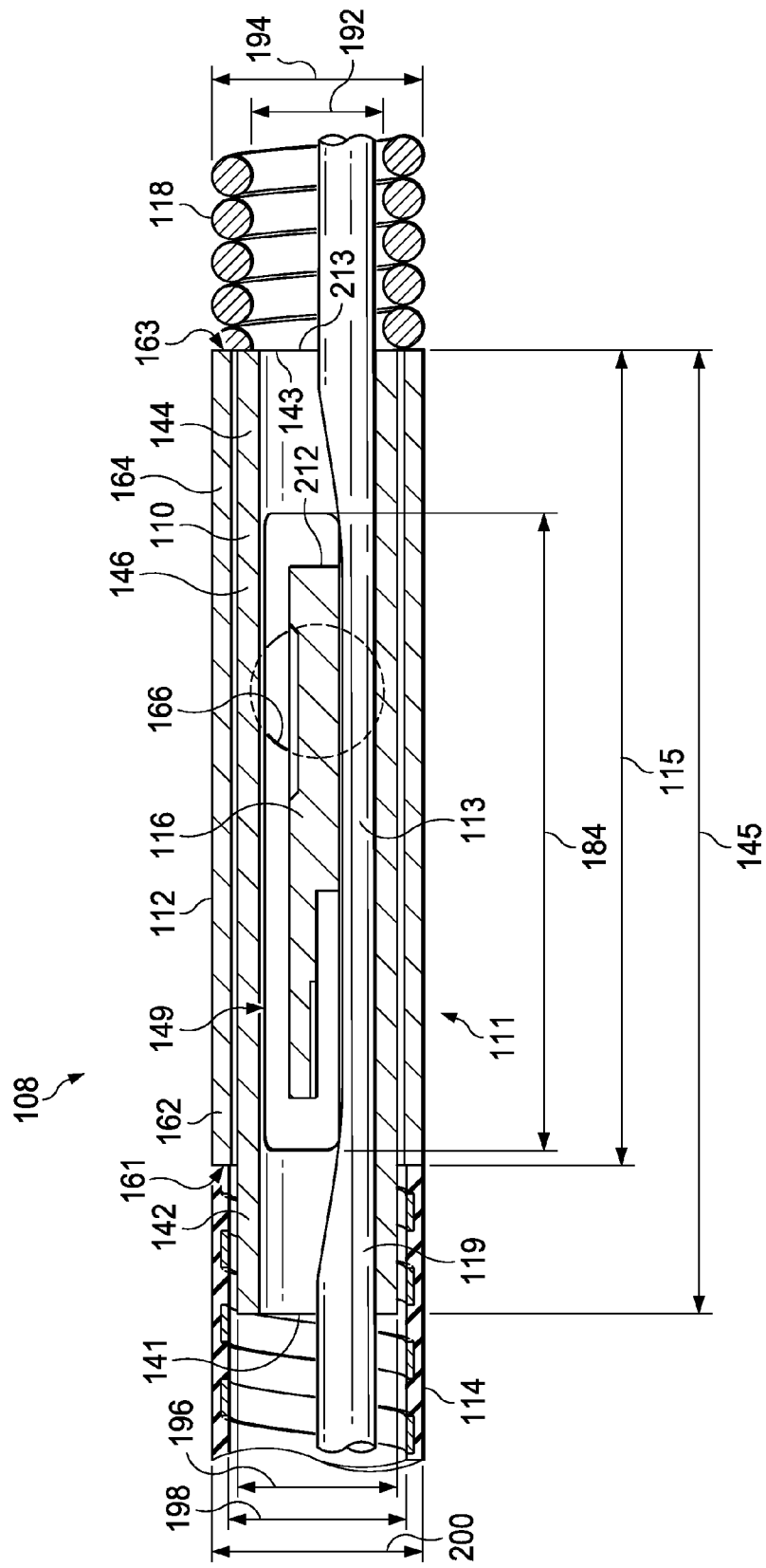
FIG. 8 illustrates a cross-sectional side view of the distal portion of the guidewire of FIG. 2 according to an exemplary aspect of the present disclosure.
Figure 11:
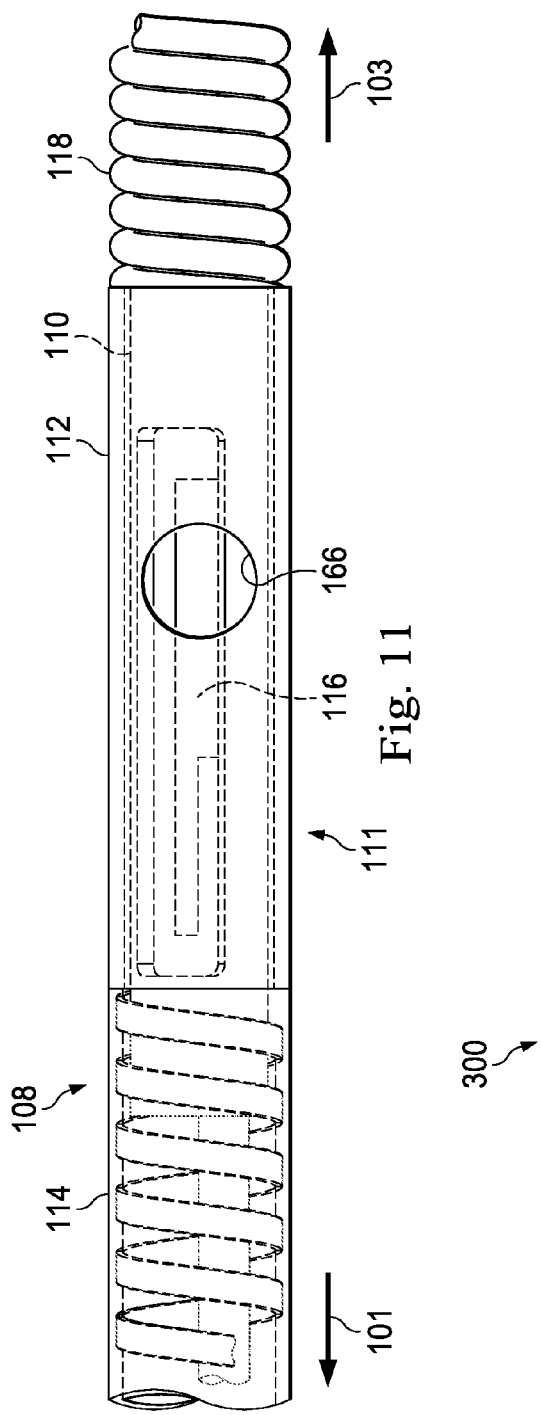
FIG. 11 illustrates a side view of a distal portion of the guidewire of FIG. 2 according to an exemplary aspect of the present disclosure.

The discussion below generally refers to FIGS. 5-11. FIGS. 5 and 6 show the internal sensor mount 110 and the sensor assembly 116 of guidewire 100. FIG. 7 is a cross-sectional end/axial view of sensor mounting assembly 111 of guide wire 100 along line 7-7 of FIG. 4. FIG. 8 is a cross-sectional side view of distal portion 108 of guidewire 100 of FIG. 7. FIGS. 9, 10, and 11 show the assembled sensor mounting assembly 111 in a top view, a perspective side view, and a side view, respectively. FIG. 10 is partially rotated about the longitudinal axis of the guidewire 110 relative to the orientations of guidewire 110 shown in FIGS. 9 and/or 11.

Internal sensor mount 110 includes a body having a proximal end 141, a proximal portion 142, a distal portion 144, and a distal end 143. Proximal portion 142 of internal sensor mount 110 extends into a volume of proximal flexible member 114 (as shown in FIG. 8). Proximal flexible member 114 and proximal portion 142 of internal sensor mount 110 are coupled using a suitable adhesive (e.g., glue, epoxy, etc.), mechanical connection, and/or combinations thereof. Distal end 143 of internal sensor mount 110 and a proximal end 213 of the distal flexible member 118 are coupled using a suitable adhesive (e.g., glue, epoxy, etc.), threading, other mechanical connection, and/or combinations thereof. As will be discussed below, in some embodiments, the distal flexible member 118 can be fixedly coupled to the external housing 112 to form a subassembly. In such embodiments, the distal flexible member 118 and the external housing 112 are collectively secured to the internal sensor mount 110. One or both of the distal flexible member 118 and the housing 112 can be fixedly secured to the internal sensor mount 110 using a suitable adhesive (e.g., glue, epoxy, etc.), threading, other mechanical connection, and/or combinations thereof.

Internal sensor mount 110 defines a lumen 152. Lumen 152 extends longitudinally along the length of internal sensor mount 110. Lumen 152 can be accessed through openings in the proximal end 141 and/or the distal end 143. Lumen 152 can also be accessed by cutouts 149 in the body of internal sensor mount 110. One or more cutouts 149 may be provided on the internal sensor mount 110 (e.g., one cutout on each of the left side and the right side of the internal sensor mount 110, when viewed from perspective shown in FIG. 7). The cutouts 149 include outer boundaries 158. The outer boundaries 158 can be the edges of the internal sensor mount 110 that immediately adjacent the cutouts 149. In some embodiments, cutouts 149 are generally rectangular-shaped such that outer boundaries 158 include two pairs of opposing sides. The sides may be joined by rounded corners. In other embodiments, cutouts 149 may take different shapes including a polygon, ellipse, and/or some combination thereof. The sensor assembly 116 can be side-loaded through one or others of the cutouts 149 before the sensor assembly is mounted in internal sensor mount 110. In some embodiments, material is removed from internal sensor mount 110 by a mechanical process (e.g., milling, laser cutting, electrical discharge machining (EDM), etc.) to form the cutouts 149 and/or other components of internal sensor mount 110. In such embodiments, the outer boundaries 158 are defined by the portions of internal sensor mount 110 that are immediately adjacent to cutouts 149 and that are left over from the mechanical process that forms cutouts 149. In other embodiments, internal sensor mount 110 is initially formed with the cutouts 149 (through, e.g., injection molding, etc.). The cutouts 149 are disposed on either lateral side of internal sensor mount 110. In various embodiments, one, two, three, or more cutouts 149 are provided. The cutouts 149 can be variously positioned along the length 145 of internal sensor mount 110. Internal sensor mount 110 has a longitudinal extent or length 145. The cutouts 149 have a longitudinal extent or length 184 (FIG. 8). The internal sensor mount 110 has a lateral extent or width 182 (FIG. 6).

Internal sensor mount 110 acts as an alignment structure for the sensor assembly 116. That is, the one or more cutouts 149 of internal sensor mount 110 are sized and shaped to help accurately align the sensor assembly 116. As discussed below, the geometry and size of the cutouts 149 can be used to locate and/or position the sensor assembly axially (or in a first dimension), the walls or lateral sides of the internal sensor mount 110 provide a visual reference for aligning the sensor assembly 116 laterally (or in a second dimension), and/or a floor or outer boundaries 158 of cutouts 149 provide a feature for aligning the sensor assembly 116 vertically (or in a third dimension). In some embodiments, the internal sensor mount 110 can include one or more alignment structures (e.g., projections, recesses, etc.) that are configured to facilitate axial, lateral, and/or vertical alignment. For example, lateral projections can be disposed across lumen 152 between cutouts 149 that are configured to interface with and axially position sensor block 212. For example, longitudinal projections can extend from a floor and/or outer boundaries 158 of internal sensor mount 110 that are configured to interface with and laterally position sensor block 212. For example, as described in U.S. Provisional Application No. 61/747,125, filed Dec. 28, 2012, the entirety of which is hereby incorporated by reference, the internal sensor mount 110 can include one or more cutouts at different vertical levels that are configured to interface with and vertically position sensor block 212. Thus, cutouts 149 of the internal sensor mount 110 can facilitates alignment in a first direction and a body of the internal sensor mount 110 can facilitate alignment in at least one of a second direction and a third direction.

The sensor assembly 116 can be aligned axially, laterally, and/or vertically relative to internal sensor mount 110. In that regard, the sensor assembly 116 is axially aligned within the length 184 of the cutouts 149 (as shown in, e.g., FIGS. 6 and 8). For example, an operator can visually inspect the placement of sensor assembly 116 within internal sensor mount 110 from the perspective shown in FIGS. 6 and/or 8. In some embodiments, the sensor assembly 116 is axially aligned when equal amounts of outer boundaries 158 are disposed on either longitudinal side of sensor assembly 116, while in other embodiments, the sensor assembly 116 is aligned when positioned more proximally or more distally. For example, a distal end of the sensor block 212 can be aligned with a distal portion of outer boundaries 158 of cutouts 149. That is, sensor block 212 can be positioned more to the left or to the right when internal sensor mount 110 is viewed in the perspective shown in FIG. 6. The sensor assembly 116 is laterally aligned within the width 182 of internal sensor mount 110 (as shown in, e.g., FIGS. 6 and 7). For example, an operator can visually inspect the placement of sensor assembly 116 from the perspective shown in FIG. 6. The sensor assembly 116 is laterally aligned when lateral sides of sensor assembly 116 do not extend beyond walls or lateral sides of internal sensor mount 110, or equally spaced from the lateral sides. In some embodiments, when the sensor assembly 116 is axially and laterally aligned, the sensor assembly does not extend beyond a volume of internal sensor mount 110. As a result, the external housing 112 can disposed around at least a portion of the internal sensor mount 110 without disrupting the mounting of the sensor assembly. For example, the external housing 112 can be slid over the internal sensor mount 110 with the sensor assembly 116 mounted in an interior of the internal sensor mount without being impeded during longitudinal displacement by any portion of the sensor assembly.

Internal sensor mount 110 includes a support member 146 that is disposed laterally between the cutouts 149. Support member 146 extends longitudinally from a proximal portion 142 to a distal portion 144 of internal sensor mount 110. Support member 146 is configured to improve structural integrity of the mount, which may be lessened because of the cutouts 149. In some embodiments, internal sensor mount 110 includes two or more support members. In some embodiments, internal sensor mount 110 includes one cutout 149, and support member 146 may be omitted. For example, the support member 146, which can include an extent between proximal and distal dashed lines shown in FIGS. 5 and 6, need not be included in internal sensor mount 110. In other embodiments, internal sensor mount 110 may include the support member 146 as a break away feature. For example, internal sensor mount 110 may be manufactured with the support member 146 (e.g., to maintain the structural integrity of the internal sensor mount 110 during manufacture). The support member 146 may be removed during a guidewire assembly process (e.g., before fixedly securing the sensor assembly 116, the external housing 112, etc.) when it is no longer required. In that regard, proximal and distal ends of the support member 146 may be scored as indicated by the dashed lines in FIGS. 5 and 6, and/or otherwise partially detached from the internal sensor mount 110 to facilitate complete removal the support member 146 when desired.

Sensor assembly 116 is mounted within a volume of internal sensor mount 110. A portion of outer boundaries 158 can be described as rails on which the sensor assembly 116 is seated. Outer boundaries 158 include rails 148. Rails 148 may include one side and/or edge of the outer boundaries 158. For example, rails 148 may include a bottom, long side and/or edge of the outer boundaries 158 (e.g., when internal sensor mount 110 is viewed from the perspective shown in FIG. 5). As shown in, e.g., FIGS. 5 and 7, lateral sides of sensor block 212 are respectively positioned on rails 148. In some embodiments, rails 148 are coplanar with the interface side 130 of the sensor block 212. That is, portions of the interface side 130 of sensor block 212 contact and/or otherwise engage rails 148. In other embodiments, a sensor side or lateral side of sensor block 212 engages rails 148. The sensor block 212 and the rails 148 are fixedly secured using a suitable adhesive (e.g., glue, epoxy, etc.), mechanical connection, and/or combinations thereof. The sensor assembly 116 can be coupled within internal sensor mount 110 such that the sensor assembly is axially and/or laterally aligned.

In some embodiments, the sensor assembly 116 is mounted within internal sensor mount 110 such that the interface side 130 is in contact with one or more filling layers of solder, an adhesive (e.g., glue, epoxy, etc.), and/or combinations thereof. For example, space 200 of internal sensor mount 110 is filled with solder and/or an adhesive material, in some instances. Space 200 can be defined as an extent between an interior (e.g., bottom) surface of internal sensor mount 110 and the interface side 130 of sensor assembly 116. Space 200 can include an extent between the interface side 130 and the reduced profile section 113 of core wire 119. The one or more filling layers of solder and/or adhesive can be provided in space 200 such that the layers form a mounting surface (e.g., a top, flat surface) on which the sensor block 212 can be positioned. In that regard, sensor block 212 is positioned within internal sensor mount 110 such that the interface side 130 contacts the solder/adhesive in space 200 and is adhered to the internal sensor mount 110. One or more filling layers of solder, adhesive, and/or combinations thereof can be used to form a solid or a relatively softer filling for space 200. For example, a first filling layer of solder, adhesive, and/or a combination thereof can be provided in space 200. A second filling layer of solder, adhesive, and/or a combination thereof can be provided on top of the first filling layer. Sensor block 212 can be positioned on top of the second filling layer (e.g., on a mounting surface defined by the second layer). In one embodiment, the first filling layer may be solid and the second filling layer may be relatively softer than the first layer. Mechanical connections and/or a combination of solder/adhesives and mechanical connections can also be provided in space 200. The mounting scheme utilizing space 200 can be implemented in addition to or in lieu of the mounting scheme in which the sensor block engages the rails 148. For example, some portions of interface side 130 can be coupled to solder/adhesive and/or mechanical connections in space 200, and some portions of interface side 130 can be coupled to solder/adhesive and/or mechanical connections on rails 148.

Sensor assembly 116 can be mounted such that it makes contact only with solder/adhesive or it can be mounted to contact both the rails 148 and the solder/adhesive in space 200. In some embodiments, one or more layers of solder/adhesive material may be provided in space 200 such that a top surface of the solder/adhesive material is at or near the vertical position of the rails 148 (e.g., the solder/adhesive material is vertically aligned with the rails 148). In such embodiments, sensor assembly 116 is likely to make contact with both the rails 148 and the solder/adhesive. A vertical position of the rails 148 may be used to level the solder/adhesive material in space 200 if the solder/adhesive material unintentionally extends beyond the vertical position. For example, an operator can remove the excess solder/adhesive material during assembly such that the top surface is at the level of the rails 148. In some embodiments, a top (e.g., mounting) surface of one or more layers of solder/adhesive material is positioned higher than or above a vertical position of the rails 148. In such embodiments, sensor assembly 116 can be described as floating in the sense that the sensor assembly is contacts only the solder/adhesive and not the rails 148.

The core wire 119 that extends longitudinally through guidewire 100 can have a section 113 with a reduced profile extending along internal sensor mount 110. For example, as shown in, e.g., FIGS. 7 and 8, a diameter of the core wire 119 is reduced (compared to the diameter of core wire 119 along other portions of guidewire 100) in a section 113 that extends generally along internal sensor mount 110. In some embodiments, the height of core wire 119 gradually decreases when moving in the distal direction from proximal flexible member 114 to the section 113. The diameter of the core wire 119 gradually increases when moving further in the distal direction away from the section 113. (The gradual decrease and increase in diameter also occurs when moving proximally from the distal flexible member 118 to section 113 and proximally away from section 113.) In other embodiments, a portion of core wire 119 is cut and/or otherwise removed to define the section 113. For example, as shown in FIG. 7, a portion large enough to accommodate the sensor block 212 is removed from core wire 119 such that sensor block 212 can be engaged with rail 148 and/or a solder/adhesive material in a planar orientation.

As shown in FIGS. 7 and 8, the internal sensor mount 110 has an outer diameter 196 and an inner diameter 195. The external housing 112 has an inner diameter 198 and an outer diameter 200. The distal flexible member 118 has an inner diameter 192 and an outer diameter 194. In some embodiments, the inner diameter 192 of the distal flexible member 118 is smaller than the outer diameter 196 of the internal sensor mount 110. This difference in diameter allows for the internal sensor mount 110 to serve as a mechanical stop as the distal flexible member 118 and/or the external housing 112 are brought into engagement with the internal sensor mount 110. In some embodiments, the external housing 112 is slid in a proximal direction 101 over the internal sensor mount 110; then, the distal flexible member 118 is brought into engagement with internal sensor mount 110 in a proximal direction 101. In other embodiments, a subassembly including the external housing 112 and the distal flexible member 118 is formed when the two are coupled. The subassembly is then brought into engagement with the internal sensor mount 110 in a proximal direction 101. In these embodiments and others, a proximal end 213 of distal flexible member 118 is prevented from further displacement in the proximal direction 101 when the proximal end 213 contacts the distal end 143 of the internal sensor mount 110. In particular, a portion of the distal flexible member 118 with a diameter that is less than the outer diameter 196 of the internal sensor mount 110 contacts the distal end 143 of the internal sensor mount 110.

When assembled, the sensor assembly 116 is mounted in internal sensor mount 110. The external housing 112 is positioned around internal sensor mount 110. One or more openings 166 of external housing 112 are disposed adjacent to the sensor assembly 116 and/or diaphragm 210 such that an interior of internal sensor mount 110 and/or external housing 102 are in fluid communication with an exterior. In the illustrated embodiments (e.g., FIGS. 9, 10, and 11), external housing 112 includes two openings 166. In other embodiments, one, two, three, four, or more openings 166 are provided. The openings 166 can be disposed to lateral sides of the external housing 112. Including multiple openings 166 and distributing them on both lateral sides ensures that measurement of the physiological characteristic (e.g., pressure) is not impeded even when sensor mounting assembly 111 is pressed against a vessel wall inside a patient's vasculature.

Figure 12:
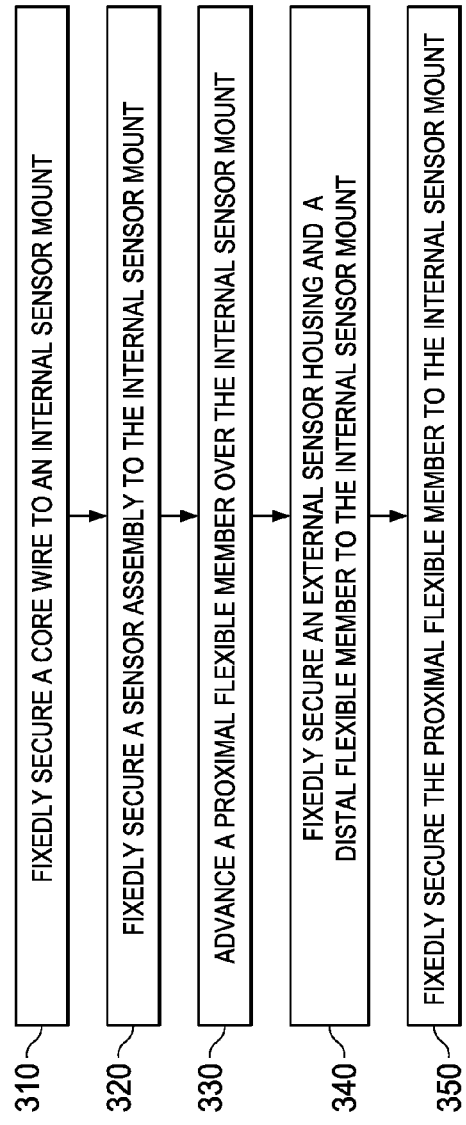
FIG. 12 is a flow diagram of a method of building a guidewire according to an exemplary aspect of the present disclosure.

FIG. 12 is a flow diagram of a method 300 of assembling a guidewire according to an exemplary aspect of the present disclosure. Assembly of the guidewire 100 may include obtaining one or more components or elements discussed herein. At step 310, method 300 includes fixedly securing a core wire to an internal sensor mount. For example, core wire 119 is fixedly secured to internal sensor mount 110. Core wire 119 can include a reduced profile portion 113 that has a smaller profile compared to other portions of core wire 119. The reduced profile portion 113 can be generated by grinding, cutting, flattening, and/or otherwise mechanically or chemically acting upon core wire 119. Reduced profile portion 113 can be aligned with the internal sensor mount 110. For example, as shown in FIG. 8, reduced profile portion 113 is axially centered relative to internal sensor mount 110 along a longitudinal axis of guidewire 100. In other embodiments, reduced profile portion 113 can be aligned relative to the proximal end 141, the distal end 143, cutout 149, rails 148 and/or other structural features of internal sensor mount 110. For example, reduced profile portion 113 can be axially positioned based on rails 148 such reduced profile portion 113 is centered relative to rails 148. Core wire 119 may extend through the internal sensor mount 110 such that a portion of the core wire is proximal of the internal sensor mount and a portion is distal of the internal sensor mount. In other embodiments, the core wire 119 can terminate within the internal sensor mount 110, and a separate core wire can be used distal of the internal sensor mount. Core wire 119 can be fixedly secured to internal sensor mount 110 using solder, weld, adhesive, and/or other suitable coupling mechanisms.

At step 320, method 300 includes fixedly securing a sensor assembly to the internal sensor mount. For example, sensor assembly 116 is fixedly secured to the internal sensor mount 110. One or more conductors of the sensor assembly 116 can be introduced through one or more cutouts 149 in the sidewall(s) of the internal sensor mount 110. The one or more conductors can be passed through a proximal lumen opening (e.g., at proximal end 141 of the internal sensor mount 110). In some embodiments, the one or more conductors are already attached or otherwise electrically coupled to the sensor assembly 116 when introduced through the one or more cutouts 149 of internal sensor mount 110. In other embodiments, the one or more conductors are not so coupled when introduced into the internal sensor mount 110. In such embodiments, the one or more conductors may be later coupled to the sensor assembly 116. For example, the sensor assembly 116 can be first introduced into an interior of the internal sensor mount 110. Then, the distal end of the one or more conductors can be passed through the proximal lumen opening at the proximal end 141 of the internal sensor mount 110. The distal end of the one or more conductors can then be attached or otherwise electrically coupled to the sensor assembly 116. In this manner, the full length of the one or more conductors is not pulled through the internal sensor mount 110. This advantageously reduces the potential for damage as a result of contact between the one or more conductors and the internal sensor mount.

The sensor assembly 116 can be disposed within the internal sensor mount 110 adjacent to the one or more cutouts 149. Once in an interior of internal sensor mount 110, sensor assembly 116 can be aligned. Sensor assembly 116 can be axially, laterally, and/or vertically aligned based on the one or more cutouts 149, proximal end 141, distal end 143, and/or other structural features of the internal sensor mount 110. In some embodiments, a temporary outer sleeve is placed around the internal sensor mount 110 to align sensor assembly 116. For example, the temporary outer sleeve may laterally center the sensor assembly 116 within the internal sensor mount 110 such that sensor assembly does not extend beyond the sidewalls of the internal sensor mount.

Adhesives and/or other suitable mechanisms may be used to secure the sensor assembly 116 in place within the internal sensor mount 110. In some embodiments, the adhesive can be disposed between the rails 148 and the sensor assembly 116 (e.g., between the bottom of the sensor assembly 116 and the rails 148). In such embodiments, there may be an open space between the bottom of the sensor assembly 116 and a floor of the internal sensor mount 110. In other embodiments, the adhesive extends from the floor of the internal sensor mount 110 to the bottom of the sensor assembly 116 (e.g., in the space 200 of FIG. 7). In embodiments in which the temporary outer sleeve is used, the temporary outer sleeve can be removed once the adhesive is sufficiently cured to hold the sensor assembly 116 in place. Once fixedly secured in an interior of the internal sensor mount 110, the sensor assembly 116 is at least partially surrounded by the internal sensor mount 110 and protected from damage that might result during further guidewire assembly steps. That is, damage that would occur as a result of, e.g., unintended contact between the sensor assembly 116 and a component (e.g., one or more conductors) may be prevented because such contact is more likely to involve the internal sensor mount 110 that surrounds the sensor assembly, rather than the sensor assembly directly. In some embodiments, the sensor assembly 116 is secured within the internal sensor mount 110 before the one or more conductors are attached or otherwise electrically coupled to the sensor assembly. In such embodiments, securing the sensor assembly 116 first can ease the process of coupling the one or more conductors to the sensor assembly because an operator can handle the relatively larger internal sensor mount 110, rather than the sensor assembly 116 directly.

At step 330, method 300 includes advancing a proximal flexible member over the internal sensor mount. For example, the proximal flexible member 114 can be advanced over the internal sensor mount 110. Proximal flexible member 114 is advanced proximally from the distal end 143 of the internal sensor mount 110 over the internal sensor mount until the distal end of the proximal flexible member 114 is positioned proximally of the proximal end 141 of the internal sensor mount. When the proximal flexible member 114 is so positioned, the core wire 119 and the one or more conductors are received within the proximal flexible member. In some embodiments, the proximal flexible member 114 is fixedly secured to the internal sensor mount 110 using solder, weld, adhesive, and/or other suitable mechanism. For example, adhesive may be used when proximal flexible member 114 is a polymer tube (which may be coil-embedded or not). In some embodiments, the proximal flexible member 114 is not fixedly secured to the internal sensor mount at step 330. As described below, the proximal flexible member 114 can be secured later, after external housing 112 is fixedly secured to the internal sensor mount 110.

At step 340, method 300 includes fixedly securing an external housing and a distal flexible member to the internal sensor mount. For example, the external housing 112 and the distal flexible member 118 are fixedly secured to the internal sensor mount 110. In some embodiments, the external housing 112 and the distal flexible member 118 are preassembled as a subcomponent. That is, the external housing 112 can be fixedly secured to the distal flexible member 118 using solder, weld, adhesive, and/or other suitable mechanism. In other embodiments, the external housing 112 and the distal flexible member 118 are individually secured to the internal sensor mount 110. The subcomponent, the external housing 112, and/or the distal flexible member 118 can be fixedly secured to the internal sensor mount 110 using solder, weld, adhesive, and/or other suitable mechanism. In various embodiments, when the subcomponent, the external housing 112, the distal flexible member 118, and/or the internal sensor mount 110 are secured in this manner, a distal portion of core wire 119 and/or a separate core wire extends through the distal flexible member 118. Once the external housing 112 is fixedly secured, the sensor assembly 116 is further protected from unintended damage because the sensor assembly 116 is additionally surrounded by the external housing 112.

Axial alignment of the external housing 112 and the distal flexible member 118 relative to the internal sensor mount 110 can be achieved through contact of the proximal end 213 of the distal flexible member and the distal end 143 of the internal sensor mount. For example, the external housing 112 can be positioned relative to the internal sensor mount 110 such that one or more openings 166 of the external housing are in communication with the one or more cutouts 149 of the internal sensor mount and/or the sensor assembly 116. The external housing 112 is advanced proximally from the distal end 143 of the internal sensor mount 110 over the internal sensor mount until the proximal end 213 of the distal flexible member 118 abuts the distal end 143 of the internal sensor mount. Further proximal displacement of the external housing 112 and the distal flexible member 118 relative to the internal sensor mount 110 is stopped when the proximal end 213 of the distal flexible member 118 contacts the distal end 143 of the internal sensor mount 110. That is, internal sensor mount 110 is a mechanical stop or mechanical limit to aid in consistently placing the external housing 112 at the same axial position relative to internal sensor mount 110 from guidewire to guidewire. The external housing 112 may be rotationally aligned with internal sensor mount 110 such that one or more openings 166 are positioned adjacent to the one or more cutouts 149 of the internal sensor mount 110 and/or the sensor assembly 116.

At step 350, method 300 includes fixedly securing the proximal flexible member to the internal sensor mount. For example, in embodiments in which the proximal flexible member 114 is not previously secured to the internal sensor mount 110 (e.g., at step 330 when the proximal flexible member is advanced over the internal sensor mount), the proximal flexible member and the internal sensor mount are secured at step 350. The proximal flexible member 114 is advanced distally over a portion of the internal sensor mount 110 (e.g., the proximal portion 142) until the distal end of the proximal flexible member contacts the proximal end 161 of the external housing 112. That is, external housing 112 is a mechanical stop or mechanical limit to aid in consistently placing the proximal flexible member 114 at the same axial position relative to internal sensor mount 110 and/or external housing 112 from guidewire to guidewire. In some embodiments, the proximal flexible member 114 is fixedly secured to the internal sensor mount 110 and/or the external housing 112 using solder, weld, adhesive, and/or other suitable mechanism. For example, adhesive may be used when proximal flexible member 114 is a polymer tube (which may be coil-embedded or not). Additionally, a thin polymer coating or sleeve (e.g., parylene, polyimide, etc.) can be positioned around the transition between the proximal flexible member 114 and external housing 112 to provide a smooth transition (eliminating any edges that could get caught on patient anatomy) and seal the connection between the proximal flexible member and the external housing.

It is understood that additional steps can be provided before, during, and/or after the steps of method 300, and some of the steps described can be replaced or eliminated in other embodiments of the method. Further, the method 300 can includes steps involved in coupling the distal portion 108 of the guidewire with one or more elements in the proximal portion 106 to form a complete guidewire 100 similar to those illustrated in FIGS. 1 and 2, for example. For example, one or more elements in the distal portion 108 can be coupled to electrical interface 122 in the proximal portion 106 in accordance with method 300. In this manner, a complete guidewire 100 for use within an anatomy of a patient may be formed via method 300.

Referring to FIGS. 13 and 14, shown therein is a sensor mounting assembly 111 at the distal portion 108 of a guidewire (e.g., the guidewire 100), according to an exemplary aspect of the present disclosure. The embodiment of FIGS. 13 and 14 can be similar to the embodiments of FIGS. 3-11. For example, the sensor mounting assembly 111 includes the external housing 112 and the internal sensor mount 110. The external housing 112 and/or the internal sensor mount 110 can be coupled to the distal flexible member 118. For example, the distal end 163 of the external housing and/or the distal end 143 of the internal sensor mount 110 can be fixedly coupled to the proximal end 213 of the distal flexible member 118. The external housing 112 and/or the internal sensor mount 110 can also be coupled to a proximal flexible member (e.g., the proximal flexible member 114). For example, the proximal end 161 of the external housing 112 can be fixedly coupled to a distal end of the proximal flexible member. The proximal end 141 and/or the proximal portion 142 can be fixedly coupled to the distal end of the proximal flexible member. A core wire can extend through the sensor mounting assembly 116, and can be secured to the internal sensor mount 110. Conductors 250 can be electrically coupled to the sensor assembly 116 (e.g., the contacts 214) and extend proximally beyond the internal sensor mount 110 through the proximal flexible member. Any suitable sensor assembly 116 can be provided at the distal portion 108.

The body of the internal sensor mount 110 of FIGS. 13 and 14 can include a cutout 149. The cutout 149 can open at least a portion (e.g., the top portion in the orientation illustrated in FIGS. 13 and 14) of the internal sensor mount 110 to the surrounding environment. For example, the internal sensor mount 110 can include a bottom portion, while the cutout 149 occupies the lateral and top portions (e.g., in the orientation illustrated in FIGS. 13 and 14). Thus, fluid, such as blood, can easily access and contact the diaphragm 210 of the sensor assembly 116 (e.g., via the openings 166 of the external housing 112). As described above, the internal sensor mount 111 can include one, two, three, or more cutouts 149 in various embodiments. FIGS. 13 and 14 illustrate and embodiment with one cutout 149, while FIGS. 3-11 illustrate embodiments with two cutouts 149. A portion of the internal sensor mount 110 can be cylindrical, while another portion can be semi-cylindrical. For example, the distal portion 144 of the internal sensor mount 110 can be cylindrical, while the remainder of the internal sensor mount 110 can be semi-cylindrical as a result of the cutout 149. In that regard, the distal portion 144 can have a height 254, while the proximal portion 142 has a height 252.

The outer boundaries 158 are the edges of the internal sensor mount 110 immediately adjacent the cutout 149. The outer boundaries 158 can be present on the top and lateral portions of the internal sensor mount 110 (e.g., in the orientation shown in FIGS. 13 and 14). Outer boundaries 158 include the rails 148, on which at least a portion of the sensor assembly 116 is seated. The sensor assembly 116 and the rails 148 are fixedly secured to each other using a suitable adhesive (e.g., glue, epoxy, etc.), mechanical connection, and/or combinations thereof. A section of the outer boundaries 158 that are adjacent the sensor assembly 116 can be linear. Or, as shown in FIGS. 13 and 14, a section 260 that includes the rails 148 can be disposed at a different height than the height of the section 262. The section 260 can be coplanar with the sensor assembly 116, while the section 262 is not. The portion of the of the sensor assembly 116 that includes diaphragm 210 can be cantilevered because the section 262 is not coplanar. The sensor assembly 116 can also be sized and shaped such that the portion including the diaphragm 210 does not contact the outer boundaries 158 and/or the rails 148. For example, in the embodiment of FIGS. 13 and 14, the portion of the sensor assembly 116 including the diaphragm 210 is narrower than the portion including the contacts 214. The portion including the contacts 214 is seated on the rails 148 while the portion including the diaphragm 210 is cantilevered.

The external housing 112 can be positioned around the sensor assembly 116 and/or the internal sensor mount 110. One or more openings 166 in the external housing 112 provide fluid communication between the sensor assembly 116 in the chamber formed by external housing 112 and the outer environment. The semi-cylindrical portion of the internal sensor mount, as a result of the cutout 149, can facilitate the creation of similar environmental conditions (e.g., pressure of blood flow) within the chamber formed by the external housing 112 as outside of the external housing 112. The openings 166 are formed to be positioned laterally beside or adjacent to the diaphragm 210. The openings 166 can be variously sized and shaped in different embodiments. For example, the openings 166 can be shaped as squares, rectangles, circles, ellipses, other suitable shapes, and/or combinations thereof. For example, in the embodiment of FIGS. 13 and 15, the openings 166 are rectangular, while in the embodiment of FIGS. 3-11, the openings 166 are circular.

A guidewire including the sensor mounting assembly 111 of FIGS. 13 and 14 can be assembled in a similar manner as the method 300 described above and/or other suitable methods. In some embodiments, the step 320 of the method 300, which includes fixedly securing a sensor assembly to the internal sensor mount, can be simplified using the sensor mounting assembly 111 of FIGS. 13 and 14. Because a portion of the internal sensor mount 110 of FIGS. 13 and 14 is semi-cylindrically shaped (e.g., the top portion of the internal sensor mount 110 is open), the sensor assembly 116 and/or the conductors 250 can be placed (e.g., from above) into of the internal sensor mount 110. Thus, the sensor assembly 116 can be more easily positioned on the internal sensor mount 110, compared to introducing the sensor assembly 116 through an opening in the side wall of the internal sensor mount 110. Similarly, the conductors 250 can be more easily positioned because they need not be threaded through a circular proximal lumen opening or an opening in the side wall of the internal sensor mount 110. For example, the sensor assembly 116 and the conductors 250 can be first electrically coupled, and then the sensor assembly 116, with the attached conductors 250, can be laid into the internal sensor mount 110. In other embodiments, the conductors 250 are not so coupled when introduced into the internal sensor mount 110. In such embodiments, the one or more conductors 250 can be laid (e.g., from above) into the internal sensor mount 110 and electrically coupled to the sensor assembly 116 after the sensor assembly 116 is placed into the internal sensor mount 110. In either case, the conductors 250 need not to be pulled or threaded through the internal sensor mount 110, which advantageously avoids the potential for damage as a result of contact between the conductors and the internal sensor mount.

Using the internal sensor mount and/or the external housing disclosed herein may increase the repeatability and consistency of sensor placement during the manufacturing process. This may provide a more consistent product to the surgeons increasing surgeon satisfaction and simplifying the assembly process.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A guidewire system for treating a patient, comprising:
   an internal sensor mount housing having a body with a first cutout extending through a wall of the body;
   a core wire secured to the internal sensor mount housing;
   a sensor assembly for detecting a physiological characteristic of a patient secured to and disposed within the internal sensor mount housing and mounted on a first rail defined by the first cutout of the internal sensor mount housing;
   an external housing disposed about the internal sensor mount housing and including a first opening in communication with the first cutout of the internal sensor mount housing;
   a proximal flexible member secured to at least one of the internal sensor mount housing and the external housing;
   a first distal flexible member secured to at least one of the internal sensor mount housing and the external housing; and
   at least one conductor electrically coupled to the sensor assembly and extending proximally beyond the internal sensor mount housing through the proximal flexible member.

2. The guidewire system of claim 1, wherein the internal sensor mount housing includes a second cutout extending through the wall of the body.

3. The guidewire system of claim 2, wherein the internal sensor mount housing includes a support member disposed between the first and second cutouts.

4. The guidewire system of claim 2, wherein the sensor assembly is further mounted on a second rail defined by the second cutout of the internal sensor mount housing.

5. The guidewire system of claim 4, wherein an interior of the internal sensor mount housing includes a first filling layer including solder, an adhesive, or a combination thereof, and a second filling layer including solder, an adhesive, or a combination thereof, the second filling layer being disposed over the first filling layer and defining a mounting surface such that the mounting surface is disposed higher than the first and second rails, and wherein the sensor assembly is mounted on the mounting surface.

6. The guidewire system of claim 2, wherein the external housing further includes a second opening in communication with the second cutout of the internal sensor mount housing.

7. The guidewire system of claim 6, wherein the first and second openings are laterally positioned relative to the sensor assembly.

8. The guidewire system of claim 1, wherein an interior of the internal sensor mount housing includes a mounting surface defined by solder, an adhesive, or a combination thereof, the sensor assembly being mounted on the mounting surface.

9. The guidewire system of claim 1, wherein the external housing includes a plurality of openings configured to provide fluid communication between the sensor assembly and an environment outside the external housing.

10. The guidewire system of claim 1, wherein the internal sensor mount housing is formed of stainless steel.

11. The guidewire system of claim 1, further comprising a second distal flexible member secured to at least one of the internal sensor mount housing, the external housing, and the first distal flexible member.

12. The guidewire system of claim 11, wherein at least one of the proximal flexible member, the external housing, the first distal flexible member, and the second distal flexible member is formed of a radiopaque material.

13. The guidewire system of claim 12, wherein the external housing and the first distal flexible member are formed of a radiopaque material, and wherein the second distal flexible member is formed of a non-radiopaque material and disposed between the external housing and the first distal flexible member.

14. The guidewire system of claim 12, wherein the external housing is formed of a radiopaque material, and wherein the proximal flexible member includes a first segment and a second segment, the second segment being formed of a radiopaque material and the first segment being formed of a non-radiopaque material, wherein the first segment is disposed between the external housing and the second segment.

15. The guidewire system of claim 1, wherein the internal sensor mount housing is cylindrical.

* * * * *